United States Patent [19]

Burolla et al.

[11] Patent Number: 5,198,091
[45] Date of Patent: Mar. 30, 1993

[54] CAPILLARY CARTRIDGE FOR ELECTROPHORESIS

[75] Inventors: Victor P. Burolla, Livermore; Ian K. Glasgow, Palo Alto, both of Calif.

[73] Assignee: Beckman Instruments, Inc., Fullerton, Calif.

[21] Appl. No.: 614,059

[22] Filed: Nov. 13, 1990

Related U.S. Application Data

[63] Continuation of Ser. No. 188,252, Apr. 29, 1988, abandoned.

[51] Int. Cl.[5] .................. G01N 27/26; G01N 27/447
[52] U.S. Cl. ........................ 204/299 R; 204/180.1; 204/183.3
[58] Field of Search ............. 204/299 R, 183.3, 180.1

[56] References Cited

U.S. PATENT DOCUMENTS

| | | | |
|---|---|---|---|
| 3,932,264 | 1/1976 | Haruki et al. | 204/299 R |
| 3,948,753 | 4/1976 | Arlinger | 204/183.3 X |
| 4,294,799 | 10/1981 | Stephens et al. | 165/30 X |
| 4,705,616 | 11/1987 | Andresen et al. | 204/299 |
| 4,816,123 | 3/1989 | Ogan et al. | 204/183.3 |
| 5,045,172 | 9/1991 | Guzman | 204/299 R |
| 5,085,757 | 2/1992 | Karger et al. | 204/299 R |
| 5,144,139 | 9/1992 | Hillman et al. | 250/341 |

FOREIGN PATENT DOCUMENTS

0304295 2/1989 European Pat. Off. .
33861 8/1989 Taiwan .

OTHER PUBLICATIONS

F. Foret et al "On-line fiber optic UV detection cell and conductivity cell for capillary zone electrophoresis" Electrophoresis 1986 7, 430–432.

*Primary Examiner*—John Niebling
*Assistant Examiner*—John S. Starsiak, Jr.
*Attorney, Agent, or Firm*—William H. May; Paul R. Harder; Wen Liu

[57] ABSTRACT

A cartridge for holding a capillary for electrophoresis. The cartridge has a body defining a passage along which the capillary is threaded. Exits are provided on the body for extending the ends of the capillary to access external fluid sources. The same cartridge may be used for different lengths of capillaries. An aperture is provided on the cartridge for optical detection of electrophoretic separation in the capillary held in the cartridge. The cartridge may include a hollow space defined about the capillary for circulating coolant fluid.

33 Claims, 5 Drawing Sheets

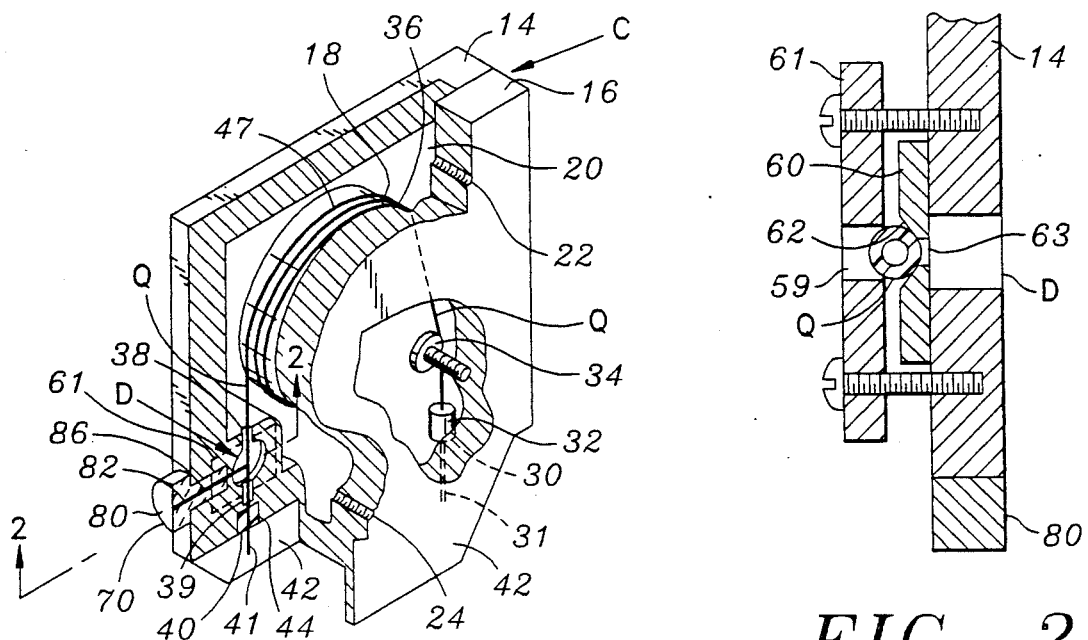
FIG. 1
FIG. 2
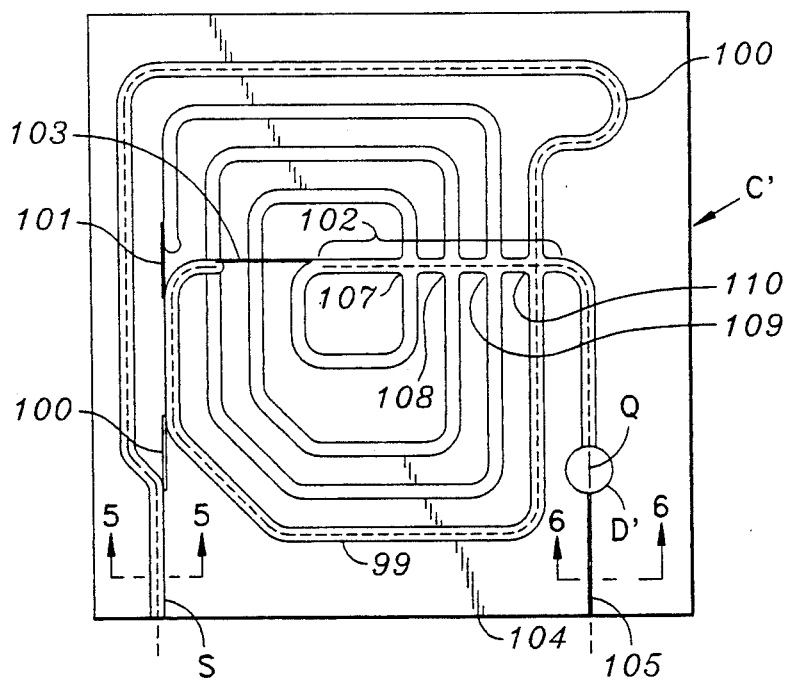
FIG. 3

CAPILLARY CARTRIDGE FOR ELECTROPHORESIS

This is a continuation of application Ser. No. 188,252, filed Apr. 29, 1988 abandoned.

BACKGROUND OF THE INVENTION

This invention relates to electrophoresis. More specifically, it relates to capillary electrophoresis where a capillary is disposed within a cartridge and the electrophoresis occurs within the capillary of the cartridge.

SUMMARY OF THE PRIOR ART

Electrophoresis is fundamentally the movement of charged particles within an applied electric field. Capillary electrophoresis is known. In this type of electrophoresis, a capillary is first filled with an electrolyte. Thereafter, sample is injected at one end of the capillary. A detector is registered to a point on the capillary typically adjacent to the other end of the capillary distant from the sample. An electropotential is applied to the capillary between the respective distal ends thereof. This electropotential is commonly applied by dipping each distal end of the capillary in a separate vial of electrolyte, with each vial being at a different electric potential.

With the electric potential applied, two separate flow effects occur.

The first of these flow effects is a gross sample flow effect. The sample moves as a mass into the capillary that was previously filled with electrolyte. Flow throughout the entire column results.

The second of these flow effects is the electrophoretic flow. This causes the constituents of the sample having differing electric charge to move relative to the main stream of fluid within the capillary.

Classification of the sample is usually detected at a detector. The detector can either measure the electrical resistance across the capillary or alternately take an optical measurement, for example, absorption or fluorescence. Likewise, measurements can include the change in the optical index of refraction (commonly referred to as Schlieren). Mass spectroscopy and other related techniques may as well be used.

Capillary electrophoresis has heretofore been a relatively difficult laboratory procedure. The capillary has to be individually cut, mechanically connected to the rest of the system and positioned with respect to a detector. Undue handling of the fragile capillary results.

Positioning of the capillary to the detector has been other than trivial. Specifically, capillaries are usually 50 microns inside diameter and 350 microns outside diameter.

These capillaries are usually protected by a protective coating. This coating first has to be removed; removal techniques include flame, heating, or chemical etching. Thereafter, the capillary has to be registered to some detector components at the section where the coating is removed. Since the capillary is very small, registration is other than trivial.

Sample has to be individually injected to the capillary. Two methods for such injection are known.

The first method requires the use of electric charge. In this method the capillary is first filled with electrolyte, an electric potential is applied from an end of a capillary immersed in sample to the opposite end of the capillary. The charge causes sample to be drawn into the capillary.

Unfortunately, with this method, the sample undergoes some classification as it enters into the capillary due to presence of the forces of electrophoresis. Hence, for many samples, insertion of the sample by electric charge is not desirable.

Additionally, sample can undergo hydrodynamic flow injection. In such injection, one end of the two ends of a capillary is raised above the other distal end of the capillary. Since the capillary has already been filled with electrolyte, flow occurs. By the expedient of immersing the raised end of the capillary in sample, flow of the sample into the capillary can occur.

Unfortunately, such a system constrains the geometry of the mechanism to which the capillary is held. For the cartridge system of holding a capillary being proposed herein, such injection is difficult. Further, trying to control the amount of sample fluid introduced precisely and reproducibility into the capillary is difficult.

It is further required that the capillary be cooled. This cooling is required because the small capillary is subject to electrical resistance heating during the period of time electrophoresis potential is applied. A small current under high voltage flowing in the capillary generates heat. There are two reasons for cooling the capillary from electrical resistance heating.

First, where the capillary can become appreciably heated the classification can be seriously degraded. Such degradation occurs by heat induced diffusion of the so-called bands of differently charged particles migrating through the capillary at different speeds. Simply stated, the heat and its resultant diffusion degrade and destroy the very classification result it is the purpose of electrophoresis to create in the first place.

Second, the heating can occur to the point where the electrolyte in the capillary vaporizes. In this case, the continuity of the electric field across the capillary is destroyed. Moreover, damage to the capillary can occur.

It is also required that remote ends of the capillary be electrically isolated. Where remote ends of the capillary come in either contact or close proximity, arcing with destruction of both the capillary and the electrophoresis in progress can occur.

SUMMARY OF THE INVENTION

A capillary for electrophoresis is disposed in a cartridge body. The cartridge body is cooled and provides a path for the capillary. The capillary is disposed over the capillary path and protrudes vertically downward from the bottom of the cartridge at two remote spaced apart locations at the bottom of the cartridge. These two remote spaced apart locations dispose the protruding capillary ends at the same elevation to restrict flow within the capillary to flow induced by electrical force or fluid pressure injection. These distal ends are sealed about their periphery with respect to the cartridge where they exit the cartridge. The distal ends protrude downwardly a sufficient distance from the bottom of the cartridge body to be able to become immersed in an electrolyte for filling the capillary (preferably at a high pressure on one end of the capillary—about 10 psi), a sample for charging the capillary (at a low measure pressure at one end of the capillary—about 1 psi) or an electrolyte at an electrical connection for causing electrophoresis in the capillary (with the same pressure at both ends of the capillary). One portion of the capillary adjacent to an end is registered to detector components defined by the cartridge. In one preferred embodiment the capillary is placed within a hollow cartridge body, spiral wound about a mandrel and cooled by a coolant, which can be forced circulated to dissipate by convection heat generated during the electrophoresis. An alternate construction includes a boron nitride block having a spiral channel. A capillary is threaded to the required length in the spiral channel, insulated at points of crossover to prevent undesired arcing, and pasted to the block with water soluble boron nitride paste. In both cases, the cartridge provides an immediately interchangeable site for electrophoresis which can conveniently be utilized for automatic electrolyte and sample injection, automated electrophoresis and automated detection without special fittings connected to the capillary. Interchanging of the cartridge permits rapid change of length, detection mode and capillaries merely by the substitution of cartridges.

OTHER OBJECTS, FEATURES AND ADVANTAGES

An object of this invention is to provide a detector cartridge for capillary electrophoresis in which the capillary is precut to a desired length, threaded over a compact path, and positioned to detector apparatus for insertion to and use in capillary electrophoresis apparatus. Accordingly, an enclosed cartridge is utilized. The cartridge defines a path for the capillary used in the electrophoresis. A precut length of capillary is positioned within the cartridge. The capillary at one end is positioned for detection through detector components in the cartridge. The capillary at its two distal ends protrudes from the bottom surface of the cartridge at two spaced apart, downwardly depending locations. Each capillary end depends a sufficient distance to enable injection of electrolyte or sample in communication with vials having electrolyte with the required electropotential therein. The periphery of the capillary is sealed to each cartridge at the exit.

An advantage of this cartridge is that it may be readily interchanged. Differing capillaries can readily be supplied by differing cartridges. Further, handling of the delicate capillary is eliminated.

A further advantage of the cartridge is that differing lengths of capillary are easily accommodated to the same size cartridge. By the expedient of winding the path back upon itself, increased lengths of capillaries can all be accommodated within the same size cartridge.

An additional advantage is that the capillary can be registered for detection adjacent to one of the two distal ends at the time the cartridge is fabricated. Consequently, the technician running samples through the electrophoresis no longer need worry about the registration of capillary to the detector.

Yet another advantage of the cartridge is that it readily accommodates all types of detection currently utilized with electrophoresis. Resistance detection, light absorption, fluorescent detection, Schlieren effect detection and mass spectroscopy can all be used. Such detectors can be positioned at one end of the capillary with the detection scheme interrupting the required cooling of the capillary over a minimal length.

An additional advantage is that portion of the detection scheme built into the cartridge can be held to a minimum. Detection apparatus utilized outside the cartridge can have most of the required complicated instrumentation affixed exterior of the cartridge. Consequently, the construction of the detector apparatus with respect to the cartridge remains simple. Complexities of detection are reserved for apparatus outside of the cartridge itself.

A further object of this invention is to seal the capillary around its periphery at its spaced apart exits from the cartridge. With seal of the periphery of the capillary to the cartridge bottom depending cartridge capillaries at their spaced apart distal ends can be immersed in liquid within the vials. The required filling of the capillaries with electrolyte and injection of sample can occur. Only the vials need be manipulated, sealed and pressurized with respect to the cartridge.

An advantage of the seal of the capillary periphery to the cartridge bottom is that the surface of the cartridge adjacent to the depending capillaries can be used as a surface against which a pressure seal can be formed. Consequently, by immersing the end of the capillary in a vial of either electrolyte or sample and sealing the vial with respect to the bottom of the cartridge, pressure injection of the electrolyte or sample is possible. Specifically, and once the seal of a vial is made, application of pressure to the inside of the sealed vial causes entrance of fluid into the capillary under pressure.

An advantage of this aspect of the invention is that the cartridge intimately participates in the injection of sample. Handling of the capillary during such injection is not required. Pressure injection to an electrophoresis capillary is vastly simplified.

A further object to this invention is to utilize the cartridge to maintain the capillary at the correct temperature for electrophoresis. According to a first embodiment of this invention, the cartridge is provided with a hollow interior. The hollow cartridge is filled with coolant. When the cartridge is in use, cooling of the capillary against the electric resistance heating caused by the electrophoresis potential occurs. This cooling occurs by the resultant convection of heat generated to the coolant.

An advantage of this aspect is that provision for the circulation of coolant may be made. Consequently, the temperature of its capillary may be maintained at predictable limits during capillary electrophoresis.

According to a second embodiment of this invention, the cartridge is fabricated from a plate of highly thermally conductive material. Such a material can include a plate of boron nitride. This boron nitride is configured from one side of the plate with a spiral channel. The capillary is threaded into this spiral channel. Once the capillary is threaded and in place in the spiral channel, it is in turn "pasted" into the groove. Such pasting preferably occurs using a water soluble boron nitride paste. The paste is molded in place, dries, and forms an integrally cooling media from the capillary to the plate.

An advantage of this aspect is that when the cartridge is in use, cooling of the capillary against electric resistance heating can occur. Simply stated, the boron nitride cartridge is registered at at least one side to a "heat sink"—such as a pure aluminum block of metal. This block of metal is preferably cooled. During electrophoresis, resistance heating is mitigated by the conduction of heat generated in the capillary through the plate of boron nitride and into the adjacent heat sink.

The advantage of this second embodiment of the invention is that the resultant heat transfer by conduction to the boron nitride has been found to be superior even to the convection. Assuming a 1.5 Kv/cm electrical potential in a 50 micron inside diameter capillary and 200–400 microamps of current, heat transfer in the solid boron carbide cartridge to temperature levels of only 10° C. difference from operating ambient temperature can be maintained. Such heat transfer can be compared to heat transfer of a capillary by a fully fluorinated coolant where capillary temperature differential is maintained at 25° C. relative to operating ambient temperature.

BRIEF DESCRIPTION OF THE DRAWINGS

Other objects, features and advantages of this invention will become more apparent after referring to the following specification and attached drawings in which:

FIG. 1 is a perspective view partially broken away of a capillary electrophoresis cartridge having a capillary depend from the cartridge at both distal ends and showing an interior mandrel for the winding of the capillary with the cartridge here containing coolant, preferably forced circulated for cooling of the capillary;

FIG. 2 is a detail of the cartridge adjacent to the detector taken along lines 2—2 of FIG. 1;

FIG. 3 is a front elevation of an alternate embodiment of the cartridge showing a solid block of conductive material configured with a spiral channel for the introduction of a capillary;

Referring to FIG. 1, cartridge C is a container approximately 4 inches by 4 inches by 1 inch thick. The cartridge is fabricated of a dielectric material. A dielectric material, such as a commercial plastic may be used.

Figure 4A:
FIG. 4A is a bottom elevation of the cartridge of FIG. 3.

The cartridge consists of two main sections. These two main sections are bonded or fastened together to create an inner chamber 20 that holds the capillary. As will hereinafter be pointed out, this inner chamber also contains a fluid to maintain a constant temperature within the capillary.

Inner portion 14 comprises the main body of cartridge C. Outer portion 16 of the cartridge C includes a coolant inlet 22 and a coolant outlet 24. The coolant can be a fluid such as distilled water or a completely fluorinated hydrocarbon. Completely fluorinated hydrocarbons are preferred over distilled water because contamination of the hydrocarbons does not as easily generate undesired conductivity of the coolant.

It will be understood that coolant circulation interior of the cartridge is not required; it is only preferred.

The capillary tube is threaded from a first aperture 30 tapped for a thread seal 32 past a bobbin 34 and onto a mandrel 36. Dependent upon the length of the capillary tube to be used, several spiral winds around mandrel 36 can occur. Capillaries of lengths from 20 cm to 100 cm have been used. Typically, the capillary tube exits mandrel 36 and thereafter passes through a seal 38 to a detector aperture D. At detector aperture D the capillary again passes through a seal 39 outwardly through aperture 40.

Once the capillary is threaded and in place, male threaded seals 32 are provided in apertures 30, 40. These seals cause a liquid tight penetration between the exterior of the capillary and the cartridge. As will hereinafter become apparent, these seals enable the cartridge to participate in the pressure injection of fluid to the capillary.

It is important to note that capillary Q at its distal ends 31 and 41 protrudes downwardly below the bottom 44 of the cartridge. To protect the protruding capillary from damage, two protective and detachably removable flaps 42 on either side of the cartridge can be utilized. These protective flaps each depending down from one side of the cartridge, prevent breakage of the protruding capillary.

Mandrel 36, like the cartridge itself, is made of dielectric material, such as a commercial plastic. It is important that the mandrel separate the coils of the capillary. For example, it is preferred that the sides of the mandrel are threaded with threads 47. These threads 47 prevent two portions of the capillary with greatly varying electrical potentials from contacting each other. Should such contact occur, the difference in electrical potential could cause an arc between respective capillary portions. Such an arc would destroy the capillary as well as destroy electrophoresis in process.

Some attention can be directed to the detector aperture D.

Referring to FIG. 2, in one embodiment used for UV absorption detection, an alignment plate 60 is provided. Plate 60 has a V groove 62, capillary Q is registered to the V groove 62. The plate also is provided with a pin hole, 63 registered to the groove. In practice this groove and pin hole have been fabricated using chemical milling technology so that registration of the capillary to the aperture is accomplished by laying the capillary in the groove.

When registration of the capillary tube to the pinhole occurs, clamping of the capillary to the plate 60 occurs, by means of a plate 61, screwed to the inner portion 14 of the cartridge C as shown in FIG. 2 (the location of the plate 61 is indicated by dotted line 61 in FIG. 1 but the details of the plate 61 have been omitted in FIG. 1 to avoid obscuring the structure of the aperture region). The plate 61 has an aperture 59. Thus light can pass from one side of the cartridge to the other side to allow optical detection of the contents flowing through the capillary.

It should be understood that the portion of the capillary tube adjacent to the detector aperture D typically has the protective coating such as a polyamide coating removed. This removal of the coating enables the silica of the capillary to be exposed for direct optical detection.

It should be understood that the detector opening in the cartridge is kept as small as possible. This is to minimize the length of the capillary that is not in contact with the coolant and therefore not cooled.

The reader will understand that the particular detector scheme utilized at aperture D may vary. In the particular detector scheme shown in FIG. 1, a protruding cylinder 80 registers the cartridge to detector apparatus (not shown). A detector aperture 82 holds a fiber optic 86 to abut the capillary Q. Light passing through the fiber optic is incident on the capillary. This light fluoresces the bands of material isolated by electrophoresis. Light passes out of the detection region outer housing 16 to a detector (not shown).

Detector aperture D can also be the light entrance for light passing through the capillary for absorption. In such case, light will pass out of the cartridge at detector aperture D in portion 14 of the housing.

Likewise, conventional electric resistance measurements can be made across the capillary. In such measurement, changing electrical resistance is measured across the capillary due to passage of classified material under electrophoresis. Similarly, measurements based upon differing optical index of refraction of the advancing classified components (Schlieren) as well as mass spectroscopy can be used.

It should be noted that the length of the capillary in the vicinity of the detector aperture D is held to a minimum. This is because coolant may not be disposed around the capillary. Consequently undesired heating may occur if the noncoolant exposed portion of the capillary is not maintained at an absolute minimum.

It will be seen that the detector is kept as close as possible to the distal end 41 of the capillary. This is to maximize the percentage length of the capillary that is used for separation. This also minimizes the voltage that needs to be applied to the entire capillary to obtain the required potential gradient in the portion of the capillary before the detector.

Having set forth an embodiment of this invention with respect to FIGS. 1 and 2, an alternate embodiment can be shown with respect to FIGS. 3-7.

Referring to FIG. 3 a cartridge C' made from a block of boron nitride is illustrated. This block is approximately 4 inches by 4 inches by 3/16th of an inch thick.

The block includes a spiral path S. Spiral path S includes multiple spiral channels configured in any desired pattern in the block. The capillary Q (represented by the dotted line) is threaded along the channels. Two constraints must be followed in the spiral path S.

Referring to the curvature 100 in the upper portion of cartridge C', the radius of curvature must be restricted to a radius wherein the capillary and its polyamide coating do not break or tear.

Second, at channels such as cross channel 102, where the channels intersect at 107, 108, 109 and 110, the depth of one of the intersecting channels should be increased. Further, and after threading a capillary Q in a channel of increased depth, a dielectric coating is required. The dielectric coating is applied before an overlapping portion of the capillary Q is threaded to the intersection at 107, 108, 109 or 110. This dielectric coating prevents the electropotential from overlapping portions of the capillary Q from arcing and destroying the desired electrophoresis.

Whereas a normal channel is 34/1000ths of an inch, a deep channel may be in the order of 64/1000ths of an inch to accommodate both the overlying capillaries and the required electrical insulation placed therebetween.

Figure 5:
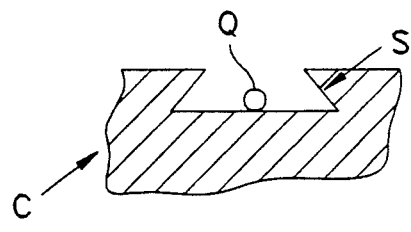
FIG. 5 is a detail of the channel in the cartridge of FIG. 3.

Referring to FIG. 5, a capillary channel having a capillary Q is illustrated at a typical section of the spiral path S. The channel is wider at the bottom than at the top. This configuration is accommodated by having an interior groove opening at an angle of 60°. This 60° opening includes 30° departure from the vertical at each of the channel side walls. This channel is uniformly configured throughout the spiral path S with the exception of the channel 105 leading from the detector aperture D' to the base 104 of the cartridge and the channels 100, 101 and 103.

Figure 6:
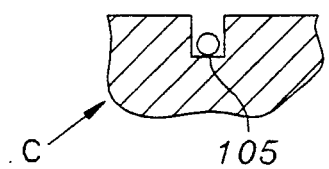
FIG. 6 is a detail of the channel adjacent to the detector of the cartridge of FIG. 3.

Referring to FIGS. 3 and 6, it can be seen that the channel 105 is configured with a square section. This channel 105 extends from the detector aperture D' to the point where the capillary Q depends from the cartridge C'. The channels 100, 101 and 103 are also narrower than the bulk of spiral path S. These channels 100, 101 and 103 are intended for use as by-pass channels connecting sections of the spiral path S for the purpose of forming a shorter path should a shorter capillary be used in the same cartridge. An example of such shorter capillary path which include channel 103 is indicated by dotted line 99 in FIG. 3.

Once the capillary Q is laid in the spiral channel to the desired length, (usually in the range of 20 to 100 cm), a boron nitride paste is applied uniformly over the channel of the spiral path S. Boron nitride paste, which is typically water soluble, dries in place leaving a solid block. This solid block having a capillary sized bore typically has a high thermal conductivity. This high thermal conductivity has been found more efficient in keeping the block cool from resistance heating encountered in the electrophoresis. (See upper right hand corner of FIG. 7)

A word can be made about the detector aperture D. Specifically, and in this embodiment, it is no longer necessary to seal the capillary Q as it crosses the aperture D'.

Further, capillary Q in crossing aperture D' is cooled at both sides immediately adjacent to the point of detection. Superior cooling results.

Figure 4B:
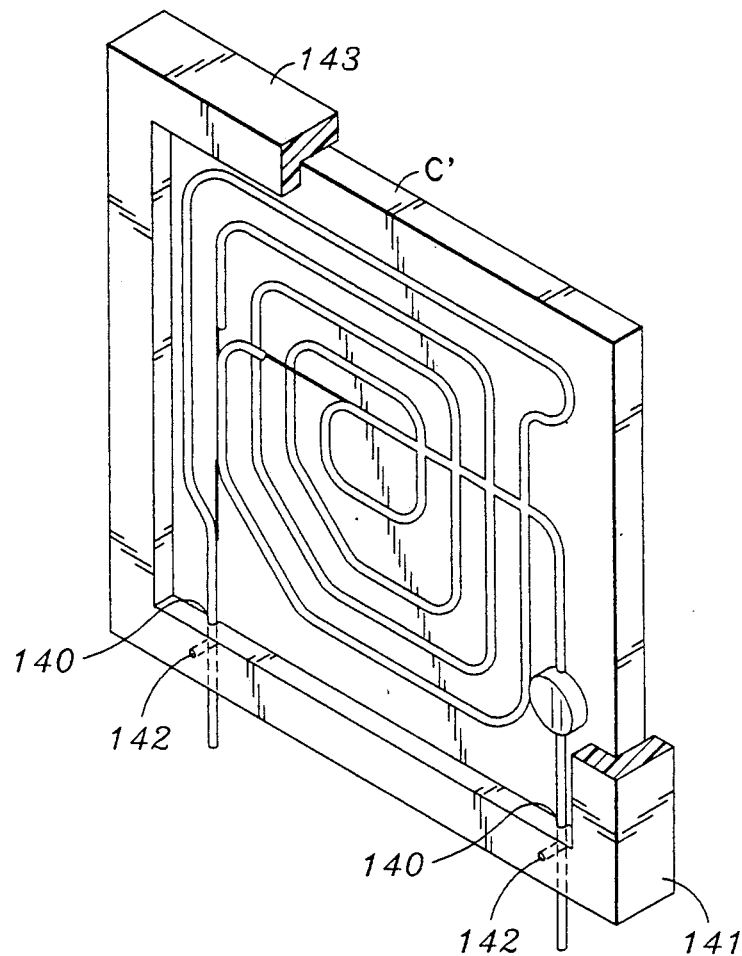
FIG. 4B is a perspective of the cartridge of FIG. 4A placed within a holder with the periphery of the capillary sealed to the holder at its point of dependency from the holder.

Referring to FIG. 4B, sealing the distal ends of the capillary to the cartridge is accomplished by inserting the boron nitride block into a plastic case 143 with apertures 140 along the bottom surface 141. As before, to effect the seal of the capillary to the bottom surface, sealant is inserted into openings 142 which communicate to apertures 140, filling the apertures.

Figure 7:
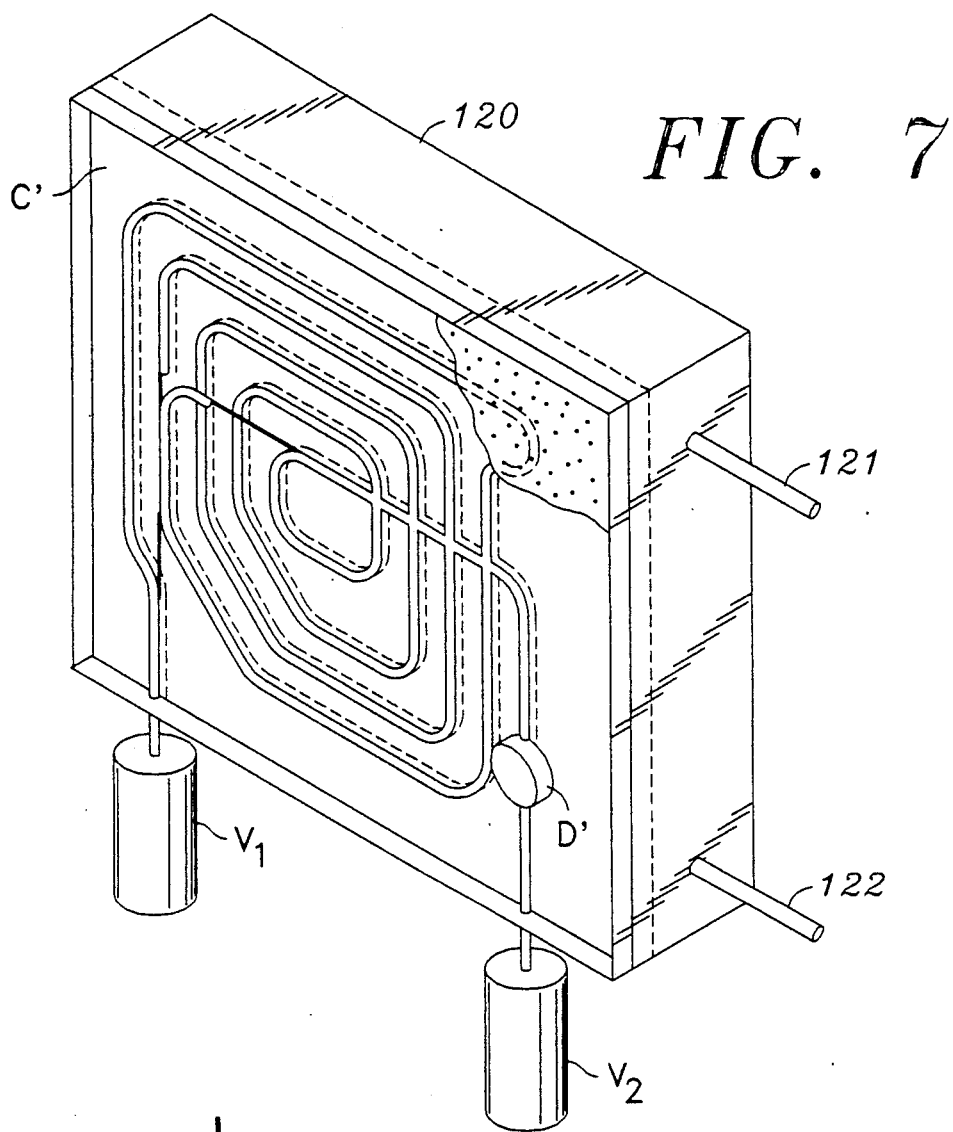
FIG. 7 is a perspective view of the cartridge of FIG. 3 utilized in an electrophoresis environment with the cartridge shown registered to a heat sink and the depending capillaries immersed in vials having either solvent or sample.

Operation of the cartridge C' can be easily understood with respect to FIG. 7. Typically, cartridge C' is registered to cooling block 120. Cooling block 120 has sources of coolant 121, 122 communicated to it. The cartridge C' is registered to one side of block 120, preferably made out of pure aluminum. Efficient cooling along the entire length of the capillary Q occurs. For example, it has been found that the solid state boron nitride block utilized enables resistance heating to be held to a level of 10° above ambient operating temperature instead of 25° for coolant convective cooling of the capillary Q.

Figure 8A:
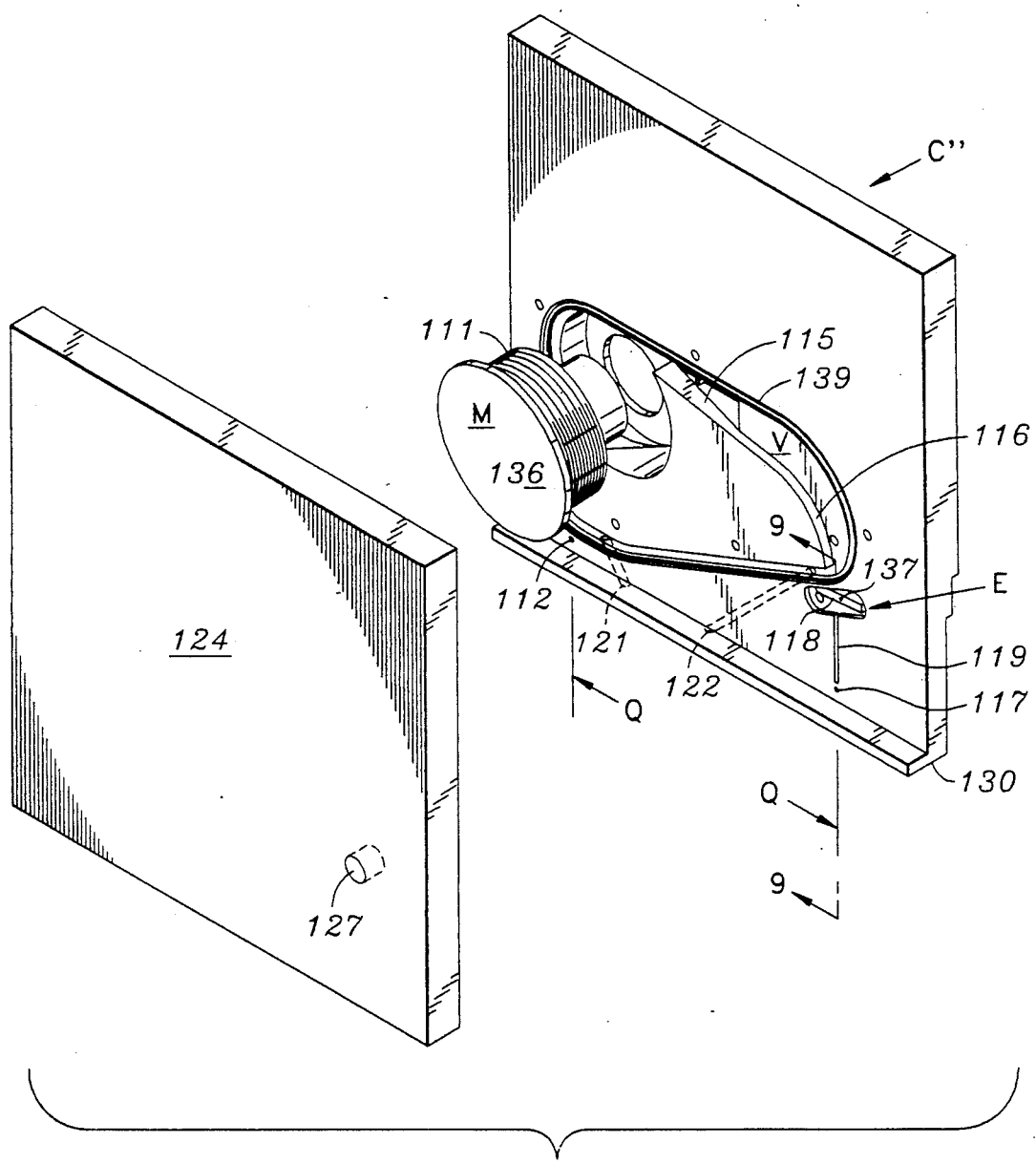
FIGS. 8A and 8B are respective front and rear perspective elevations of the presently preferred cartridge of this invention illustrating in exploded views the components of the cartridge and their relative placement; and, FIG. 9 is a detail illustrating how a seal of the capillary can be effected in the embodiment of FIGS. 8A and 8B.

Referring to FIG. 8A, the interior of the cartridge C'' is set forth. Cartridge C'' defines an interior volume V, which volume V contains coolant around capillary Q.

Capillary Q is initially threaded through air aperture passing out the bottom of the cartridge (hidden from view). The capillary is then passed a sufficient number of times around a mandrel M having helical threads Threads 111 are given sufficient depth and spacing so that remote parts of the capillary do not make electric contact or arc through the capillary during the electrophoretic process. As illustrated in the exploded perspective of FIG. 8A, the mandrel is first wound and thereafter inserted interior of the volume V in the cartridge C''.

The capillary Q typically is aligned the first wind around mandrel M. After the requisite number of turns to accommodate the intended length of the capillary the capillary passed over exit surface 115. At this surface the capillary gradually turns vertically downward departing exit surface 115 at point 116. Thereafter, the capillary passes across the detection region E along a vertical exit passage 119 and out cartridge bottom 130. The capillary Q is registered to a bar 118 within detection region E, this bar having a small central aperture 137 for the passage of light. As will hereinafter be set forth, passage of the light through the cartridge C'' at detection region E allows the classified components to be identified.

Assuming that the capillary is completely threaded interior of the cartridge C'', an O-ring 139 is thereafter threaded completely around the interior of the boundary wall of the volume V. This O-ring 139 in passing over the capillary Q, traps the capillary in place.

Once the O-ring 139 is in place, a cover 124 is placed over and sealed in position, enclosing the cartridge. (See FIG. 9 in which cover 124 is indicated by dotted outline)

Figure 8B:
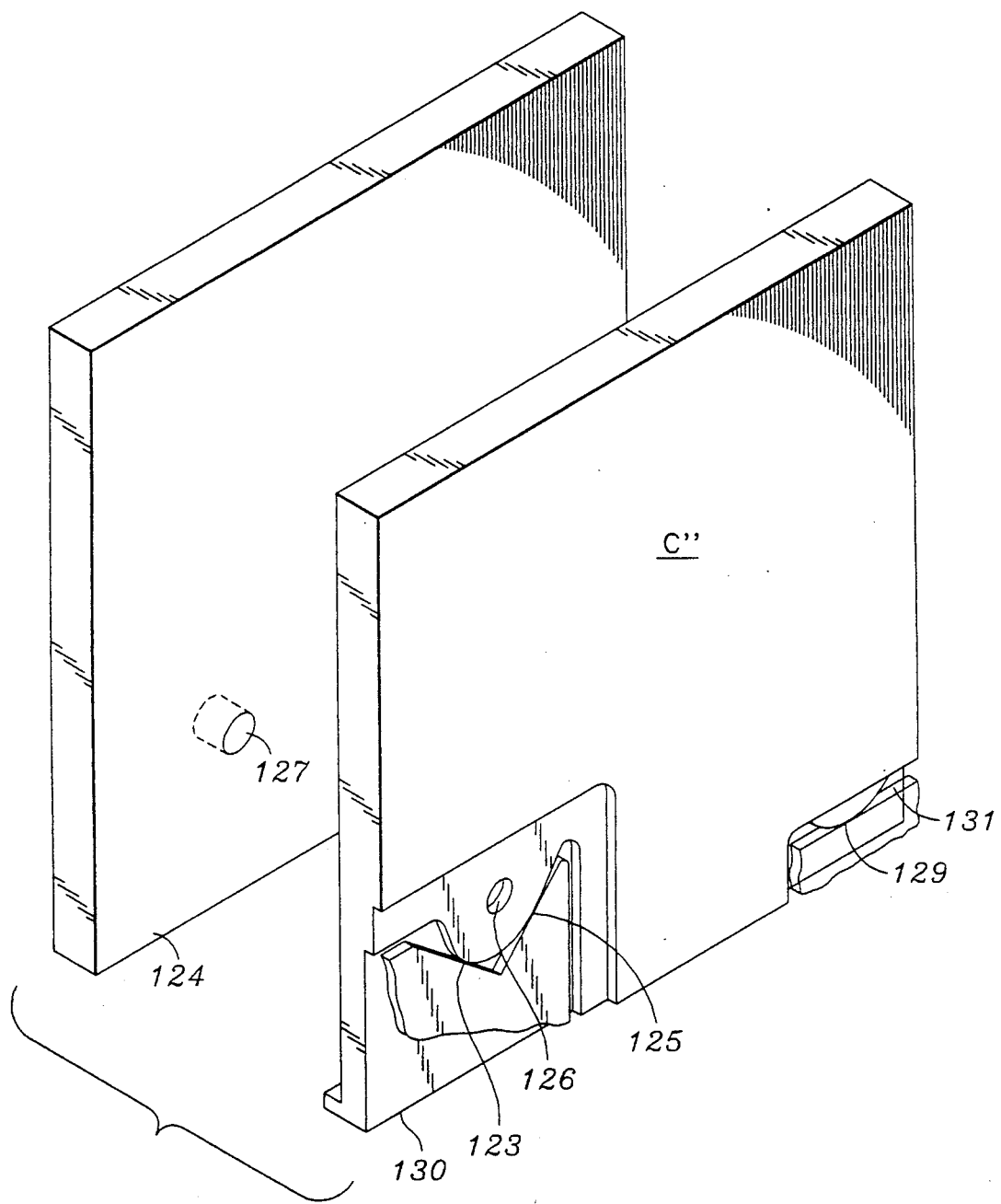

Turning to the view of FIG. 8B, the rear surface of the cartridge can be seen and understood. Detector aperture 126 has a concentric and essentially circular gathering surface 125 for aligning external optics to the aperture 126. Preferably, this circular gathering surface 125 is registered to a V-groove 123 associated with an external detection optics (not shown). Similarly, plate 124 has a similar aperture 127. Thus, when plate 124 closes the cartridge, light can pass through the cartridge and through the capillary Q for required detection of classified "bands" of like particles.

When circular gathering surface 125 is registered to a V groove, it is required the cartridge C'' be held level with respect to its bottom surface 130. Accordingly, a second round surface 129 is downwardly disposed for resting on a leveling bar 131, this leveling bar being attached to apparatus for holding the cartridge (not otherwise shown).

With the exception of the indentation of the cartridge to define gathering surface 125 and leveling surface 129, the rear of the cartridge is essentially rectilinear.

A word relating to two conduits 121 and 122 shown in broken lines in FIG. 8A. These conduits 121 and 122 are for the entry and exit of cooling fluid used during the electrophoresis within the cartridge C''. It can be seen that the conduits start at the bottom surface of cartridge C'' and extend into the volume V interior of the O-ring 139. Thus, before the electric potential is placed across the distal ends of the capillary Q, the entire volume of the cartridge C'' can be flooded with coolant. Likewise, and immediately before cartridges are removed, draining of the inner volume V can likewise occur.

Figure 9:
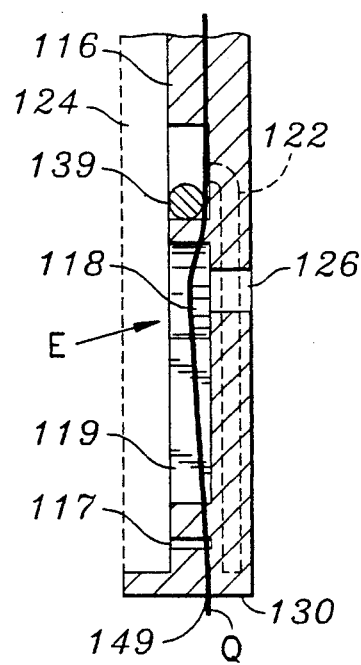

Referring to the section illustrated in FIG. 9, the detail of the sealing of the capillary Q can be seen and understood. Capillary Q is threaded out of aperture 149 of cartridge C''. In such threading it is depended the required distance below the bottom 130 of the cartridge.

Immediately before block 124 closes cartridge C'', capillary Q has sealant forced through apertures 112 and 117. Such sealant, preferably a silicon rubber compound, fills apertures 112 and 117, surrounds the capillary Q, and effects a sealing of the periphery of the capillary Q to the cartridge C. As will hereafter become more apparent, this sealing enables fluid to be forced under pressure up the interior of the capillary Q. A description of the pressure injection system is found in copending U.S. application Ser. No. 07/187,760, filed Apr. 29, 1988, which is commonly assigned to the assignee of the present invention.

What is claimed is:

1. A cartridge for electrophoresis between two fluid reservoirs comprising in combination:
    a portable cartridge body having a bottom surface;
    a capillary having a predetermined length and two distal ends for placement in said cartridge body;
    said cartridge body defining at the bottom surface thereof first and second space apart exits for disposing the distal ends of said capillary in depending relation from said body;
    said cartridge body having means for accommodating a capillary between said first and second spaced apart exit paths;
    said capillary disposed in the cartridge body with the distal ends of said capillary in depending relation from said body through the bottom of said body a distance below the bottom surface of said body to enable the penetration of the capillary ends into fluid reservoirs for the communication of said capillary to said fluid reservoirs;
    said cartridge body also having a detection path defined therein for detecting electrophoretic separation including at least one aperture from the exterior of said cartridge body to the interior of said cartridge body; and
    means for registering said capillary with said detection path to facilitate detection of electrophoretic separation in said capillary.

2. The invention of claim 1 and wherein said cartridge body define a space around the capillary which facilitates circulation of
    a coolant.

3. The invention of claim 2 and wherein said cartridge body includes a coolant inlet and a coolant outlet for the forced circulation of coolant through said cartridge.

4. The invention of claim 2 and wherein said means for accommodating includes means for supporting the capillary in the space of said cartridge.

5. The invention of claim 1 and wherein said cartridge body is solid having a side;
    and said means for accommodating is defined by the surface of a groove configured in the side of said solid cartridge body;
    said capillary being threaded along and partially filling said groove; and
    a thermally conductive material filling remaining portions of said groove to confine said capillary to said capillary path.

6. The invention of claim 4 and wherein one portion of said capillary path crosses another portion of said capillary path, one of said portions being deeper than the other of said portions.

7. A cartridge for capillary electrophoresis, said cartridge for maintaining a capillary having two spaced apart distal ends therein, said cartridge comprising in combination:
- a portable cartridge body;
- means for accommodating said capillary within said cartridge body;
- first and second exit paths in said cartridge body to enable communication of said capillary with external fluid reservoirs;
- said cartridge body also having a path defined therein for detecting electrophoretic separation including at least one aperture from the exterior of said cartridge body to the interior of said cartridge body; and
- means for registering said capillary to said path to facilitate detection of electrophoretic separation in said capillary.

8. The invention of claim 7 and wherein said means for accommodating is a capillary path configured in one side of said cartridge body.

9. The invention of claim 7 and wherein said means for accommodating includes means for supporting said capillary along a specified path.

10. The invention of claim 9 and wherein said means for supporting includes a structure for the winding of said capillary in a helical path.

11. The invention of claim 7 and wherein said cartridge body has a hollow interior;
- the cartridge body further having first and second conduits, each said conduit communicated between the hollow interior and exterior of said cartridge body whereby said conduits can be used to fill said cartridge body with coolant.

12. The invention of claim 7 further comprising means for sealing said capillary to said cartridge body at said exit paths.

13. Apparatus for electrophoresis in a capillary supported in a cartridge body, said apparatus comprising in combination:
- a capillary having two distal ends;
- a cartridge body;
- means for accommodating the capillary in said cartridge body;
- first and second spaced apart exit paths in said cartridge body to enable fluid communication of said capillary with external fluid reservoirs;
- a detection path in said cartridge body including at least one aperture defined in said cartridge body adjacent to one of said exit paths;
- means for registering said capillary to said detection path to facilitate detection of electrophoretic separation in said capillary from the exterior of said cartridge; and
- means on said cartridge for facilitating alignment of the detection path in said cartridge body with respect to an external detector.

14. The invention of claim 13 and wherein said cartridge body includes a structure which facilitates circulation of a coolant through the cartridge body.

15. A portable capillary cartridge, the cartridge comprising:
- a length of capillary having two ends; and
- a body, in which is defined a space in which the capillary is supported whereby the ends of the capillary are positioned for fluid communication with external fluid sources.

16. A portable cartridge as in claim 15 wherein the body includes means for supporting the capillary along a predetermined path.

17. A portable cartridge as in claim 16 wherein the means for supporting is a surface of the body in which is formed a groove along which the capillary is threaded.

18. A portable cartridge as in claim 17 wherein the surface is substantially planar.

19. A portable cartridge as in claim 18 wherein the groove is configured in a spiral on the surface.

20. A portable cartridge as in claim 19 wherein there is provided one or more by-pass grooves connecting different sections of the spiral so as to define a shorter passage along which a shorter length of capillary may be threaded thereby providing an option of using a capillary of a different length with the same cartridge.

21. A portable cartridge as in claim 16 wherein the means for supporting supports the capillary in a spiral configuration.

22. A portable cartridge as in claim 21 wherein the space of the body is a hollow interior within the body, and the means for supporting includes a mandrel housed in the hollow interior defined within the body.

23. A portable cartridge as in claim 22 wherein the hollow interior is sealed in a manner to allow a fluid coolant to be held in the interior.

24. A portable cartridge as in claim 23 wherein the body has an inlet and an outlet in fluid communication with the hollow interior for circulation of coolant through the hollow interior of the body.

25. A portable cartridge as in claim 15 wherein the body further includes a detection passage to enable detection of electrophoretic separation in the capillary.

26. A portable cartridge as in claim 25 further comprising an alignment means for aligning the capillary with respect to the detection passage.

27. A portable cartridge as in claim 26 wherein the alignment means includes an alignment plate having a groove for seating the capillary and an aperture transverse to the groove to allow optical detection of electrophoretic separation in the capillary, the alignment plate being positioned on the body with the aperture aligned with the detection passage.

28. A portable cartridge as in claim 15 wherein the body includes a structure which facilitates circulation of coolant through the space.

29. A portable cartridge as in claim 15 wherein the body includes means structured and configured for facilitating cooling of the capillary.

30. A portable capillary cartridge for electrophoresis comprising:
- a length of capillary having two ends; and
- a body having a space for accommodating at least a substantial section of the capillary, the body also having two exits through which the ends of the capillary maintain fluid communication with external fluid sources, and the body further having a detection passage for enabling for enabling detection of electrophoretic separation in the capillary.

31. A portable cartridge as in claim 30 wherein the body includes means structured and configured for facilitating cooling of the capillary.

32. A capillary cartridge for electrophoresis comprising:
- a length of capillary having two ends;
- a base through which the ends of the capillary are coupled for fluid communication with fluid sources; and
- means coupled to the base for defining a detection passage and for supporting at least a section of the capillary in alignment with the detection passage to enable detection of electrophoretic separation in the capillary.

33. A portable cartridge as in claim 32 wherein the body includes means structured and configured for facilitating cooling of the capillary.

* * * * *